US012544474B2

(12) United States Patent
Yoo

(10) Patent No.: US 12,544,474 B2

(45) Date of Patent: Feb. 10, 2026

(54) CANDLE WARMER WITH HEIGHT ADJUSTMENT FUNCTION

(71) Applicant: HYUNPEOPLE CO., LTD., Pocheon-si (KR)

(72) Inventor: Sung Hei Yoo, Guri-si (KR)

(73) Assignee: HYUNPEOPLE CO., LTD., Pocheon-si (KR)

( * ) Notice: Subject to any disclaimer, the term of this patent is extended or adjusted under 35 U.S.C. 154(b) by 715 days.

(21) Appl. No.: 17/894,592

(22) Filed: Aug. 24, 2022

(65) Prior Publication Data

US 2024/0066171 A1 Feb. 29, 2024

(51) Int. Cl.
*A61L 9/03* (2006.01)

(52) U.S. Cl.
CPC ............ *A61L 9/03* (2013.01); *A61L 2209/111* (2013.01); *A61L 2209/12* (2013.01); *A61L 2209/15* (2013.01)

(58) Field of Classification Search
CPC .. A61L 9/03; A61L 2209/111; A61L 2209/12; A61L 2209/15; A61L 2209/11
See application file for complete search history.

(56) References Cited

U.S. PATENT DOCUMENTS

2022/0230532 A1* 7/2022 Myoung .................. A61L 9/03

FOREIGN PATENT DOCUMENTS

KR 20-0453039 Y1 4/2011
KR 20190105826 A * 9/2019 ............ A61L 9/032

* cited by examiner

*Primary Examiner* — Brendan A Hensel

(74) *Attorney, Agent, or Firm* — Bridgeway IP Law Group, PLLC; Sang Ho Lee; Hyun Woo Shin

(57) ABSTRACT

Provided is a candle warmer with a height adjustment function, and more particularly, to a candle warmer with a height adjustment function that adjusts a height between a candle and a heating element, thus allowing a user to flexibly correspond to various forms or types of scent-releasing candles used and allowing a scent release effect to last by efficiently melting a candle even when the candle melts and shortens.

6 Claims, 12 Drawing Sheets

CANDLE WARMER WITH HEIGHT ADJUSTMENT FUNCTION

BACKGROUND

1. Field of the Invention

The present disclosure relates to a candle warmer with a height adjustment function, and more particularly, to a candle warmer with a height adjustment function that includes a base frame, a height adjustment support, a heating shade, a heating element fixer, and a heating element and adjusts a height between a candle and a heating element, thus allowing a user to flexibly correspond to various forms or types of scent-releasing candles used and allowing a scent release effect to last by efficiently melting a candle even when the candle melts and shortens.

2. Discussion of Related Art

Generally, a candle warmer is a device that uses a light source providing high-temperature heat, such as a halogen lamp, to radiate the high-temperature heat toward a candle including a scent component such as aroma and melts the top of the candle by the radiated heat to diffuse the scent included in the candle in the air.

Using such a candle warmer, there is an effect of allowing a scent of a candle to be released even when the candle is not lighted. In this way, there are advantages in that convenience in use is increased and it is possible to address a problem of spread of particulate matter due to burning a candle.

A conventional candle warmer includes a main body having one side on which a candle is mounted, a lamp disposed above the candle to emit luminescent heat, a socket configured to supply power to the lamp, a lampshade disposed in a form surrounding the lamp and the socket to concentrate light and heat emitted from the lamp, a support guide configured to allow the socket to be fastened to the lampshade, and an extension pipe formed to extend from the other side of the main body so that the support guide is disposed at a predetermined height.

Here, the conventional candle warmer is assembled by welding each fastening portion so that the socket, the lampshade, the support guide, and the extension pipe are fastened to each other. Due to the welding fastening method, there are problems that not only the product manufacturing time is increased, but also the manufacturing process becomes complex and the manufacturing cost is increased due to having to remove a dummy portion and apply a varnish to prevent oxidation of welded parts after welding.

Further, candles of various sizes with different heights are being sold in the market, and while a height of the top of a typical candle gradually decreases as the candle melts and a paraffin component evaporates therefrom, an installation position of a lamp is fixed in the conventional candle warmer, and thus there are problems that, when a candle in the candle warmer is replaced with a candle with a low height or as a height of the candle decreases with an increase in the use time, the luminescent heat transferred to the top of the candle is reduced and scent release performance is degraded.

SUMMARY OF THE INVENTION

The present disclosure is directed to providing a candle warmer with a height adjustment function that adjusts a height between a candle and a heating element, thus allowing a user to flexibly correspond to various forms or types of scent-releasing candles used and allowing a scent release effect to last by efficiently melting a candle even when the candle melts and shortens.

The present disclosure is also directed to providing a candle warmer with a height adjustment function that includes a base frame (100) having a candle mounting surface (110), on which a candle is mounted, provided at an upper portion, and a height adjustment support (200) coupled in an upright state to an upper surface of the base frame (100) behind the candle mounting surface (110) and having a power line accommodation space (210) in which a power line (610), which is installed from a power source to a heating element (500), is accommodated, thereby conveniently adjusting the height according to a use state of the candle.

The present disclosure is also directed to providing a candle warmer with a height adjustment function that includes a heating shade (300) which is connected to the height adjustment support (200) from above the height adjustment support (200) while being penetrated thereby, is formed in the shape of a bell, and has an accommodation space (310), which opens downward, provided at the center, a heating element fixer (400) having a vertical fixer (420) provided to be fixed to the heating shade (300) through an upper fixer (410), which is disposed at the center of a bottom surface of an upper portion of the heating shade (300), to fix the heating element (500), and the heating element (500) having a power connector (510), which is coupled to a longitudinal end of the vertical fixer (420) in a ground direction and connected to the power line (610), to generate heat toward a candle, thereby firmly maintaining a heat radiation angle and having high energy efficiency.

The present disclosure is also directed to providing a candle warmer with a height adjustment function in which the height adjustment support (200) includes a first support pipe (220) fixed in an upright state to a vertical coupling hole (120) disposed in the base frame (100), a second support pipe (230) inserted into the first support pipe (220) to allow a height to be adjustable, and a third support pipe (240) bent in an L-shape from a longitudinal end of the second support pipe (230) toward the heating shade (300), wherein a semi-circular guide groove (221) is formed inward in one side of at least any one of the first support pipe (220) and the second support pipe (230), and a plurality of height adjustment holes (222) are formed at predetermined intervals in the first support pipe (220), thereby allowing for adjustment to various heights by a simple operation.

The present disclosure is also directed to providing a candle warmer with a height adjustment function in which the height adjustment holes (222) each have an inclined surface (**222*a*) to be inclined upward or downward in a direction from an outer circumferential surface of the first support pipe (220) toward an inner circumferential surface thereof, a height adjustment protrusion (231) configured to protrude through the height adjustment hole (222) is provided on an outer circumferential surface of the second support pipe (230), the height adjustment protrusion (231) includes a protruding surface (231*a*), an inner spring (231*b*), and a spring guider (231*c*) configured to accommodate a portion of a longitudinal end of the inner spring (231*b*), and the spring guider (231*c*) is fixed to an inner circumferential surface of the second support pipe (230**), thereby allowing for smooth adjustment.

The present disclosure is also directed to providing a candle warmer with a height adjustment function in which the height adjustment support (200) further includes an auxiliary sliding support pipe (250) which is inserted into the first support pipe (220) from above the first support pipe (220), has a hollow formed therein, and is made of a synthetic resin, the second support pipe (230) is insertable into an upper portion of the auxiliary sliding support pipe (250), and the auxiliary sliding support pipe (250) has a sliding protrusion (251) which is disposed at an upper end and protrudes more outward than an outer diameter of the second support pipe (230) and a sliding guide pipe (252) which is disposed below the sliding protrusion (251) and inserted into the first support pipe (220), thereby allowing for smooth vertical movement.

The present disclosure is also directed to providing a candle warmer with a height adjustment function in which a first gear (223) is disposed on the outer circumferential surface of the first support pipe (220), and a lifting/lowering motor (130) and a second gear (131) which rotates due to the lifting/lowering motor (130) and is engaged with the first gear (223) are disposed on a bottom surface of the base frame (100) to allow the first support pipe (220) to move upward and downward while engaged with the first gear (223), thereby allowing a controller (600) to adjust a height according to temperatures.

The present disclosure is also directed to providing a candle warmer with a height adjustment function in which the upper fixer (410) includes a first fixer (411) coupled to the heating shade (300) while in contact therewith and a second fixer (412) configured to come in contact with a lower surface of the first fixer (411) and block heat of the heating element (500) from being transferred upward, and the vertical fixer (420) is provided to be vertically connected from a lower portion of the second fixer (412) to the heating element (500), thereby transferring the heat downward and suppressing upward movement of the heat.

Meanwhile, objectives of the present disclosure are not limited to those mentioned above, and other unmentioned objectives should be clearly understood by those of ordinary skill in the art to which the present disclosure pertains from the description below.

A candle warmer with a height adjustment function according to one embodiment of the present disclosure may include a base frame (100) having a candle mounting surface (110), on which a candle is mounted, provided at an upper portion.

In addition, the candle warmer with a height adjustment function may include a height adjustment support (200) coupled in an upright state to an upper surface of the base frame (100) behind the candle mounting surface (110) and having a power line accommodation space (210) in which a power line (610), which is installed from a power source to a heating element (500), is accommodated.

Also, the candle warmer with a height adjustment function may include a heating shade (300) which is connected to the height adjustment support (200) from above the height adjustment support (200) while being penetrated thereby, is formed in the shape of a bell, and has an accommodation space (310), which opens downward, provided at the center.

Also, the candle warmer with a height adjustment function may include a heating element fixer (400) having a vertical fixer (420) provided to be fixed to the heating shade (300) through an upper fixer (410), which is disposed at the center of a bottom surface of an upper portion of the heating shade (300), to fix the heating element (500).

In addition, the candle warmer with a height adjustment function may include the heating element (500) having a power connector (510), which is coupled to a longitudinal end of the vertical fixer (420) in a ground direction and connected to the power line (610), to generate heat toward a candle.

Also, the candle warmer with a height adjustment function may include a controller (600) provided to control on or off of power and operation of the heating element (500) through the power line (610).

Here, the height adjustment support (200) may include a first support pipe (220) fixed in an upright state to a vertical coupling hole (120) disposed in the base frame (100), a second support pipe (230) inserted into the first support pipe (220) to allow a height to be adjustable, and a third support pipe (240) bent in an L-shape from a longitudinal end of the second support pipe (230) toward the heating shade (300), wherein a semicircular guide groove (221) is formed inward in one side of at least any one of the first support pipe (220) and the second support pipe (230), a plurality of height adjustment holes (222) are formed at predetermined intervals in the first support pipe (220), the height adjustment holes (222) each have an inclined surface (222*a*) to be inclined upward or downward in a direction from an outer circumferential surface of the first support pipe (220) toward an inner circumferential surface thereof, a height adjustment protrusion (231) configured to protrude through the height adjustment hole (222) is provided on an outer circumferential surface of the second support pipe (230), the height adjustment protrusion (231) includes a protruding surface (231*a*), an inner spring (231*b*), and a spring guider (231*c*) configured to accommodate a portion of a longitudinal end of the inner spring (231*b*), and the spring guider (231*c*) is fixed to an inner circumferential surface of the second support pipe (230).

Here, the height adjustment support (200) may further include an auxiliary sliding support pipe (250) which is inserted into the first support pipe (220) from above the first support pipe (220), has a hollow formed therein, and is made of a synthetic resin, and the second support pipe (230) may be provided to be insertable into an upper portion of the auxiliary sliding support pipe (250).

Here, the auxiliary sliding support pipe (250) may have a sliding protrusion (251) which is disposed at an upper end and protrudes more outward than an outer diameter of the second support pipe (230) and a sliding guide pipe (252) which is disposed below the sliding protrusion (251) and inserted into the first support pipe (220).

Meanwhile, a first gear (223) may be disposed on the outer circumferential surface of the first support pipe (220), and a lifting/lowering motor (130) and a second gear (131) which rotates due to the lifting/lowering motor (130) and is engaged with the first gear (223) may be further disposed on a bottom surface of the base frame (100) to allow the first support pipe (220) to move upward and downward while engaged with the first gear (223).

Also, meanwhile, the upper fixer (410) may include a first fixer (411) coupled to the heating shade (300) while in contact therewith and a second fixer (412) configured to come in contact with a lower surface of the first fixer (411) and block heat of the heating element (500) from being transferred upward, and the vertical fixer (420) may be provided to be vertically connected from a lower portion of the second fixer (412) to the heating element (500).

Here, the heating shade (300) may include a first heating shade (320) configured to accommodate the heating element fixer (400) and the heating element (500) and a second heating shade (330) which extends downward from a lower edge of the first heating shade (320) and has an angle of inclination extending more outward than the first heating shade (320), and a heat reflecting shade (321) may be further disposed at an inner side of the second heating shade (330).

Meanwhile, the controller (600) may be provided to pre-store a threshold temperature in a memory (620), may be provided to compare a temperature collected by a temperature sensor and the threshold temperature stored in the memory (620) and, in a case in which the collected temperature is higher than or equal to the threshold temperature, turn off the power, and may be provided to send the collected temperature to the outside through a communication device (630), a maximum power-on time may be pre-registered in the memory (620), and upon the power being turned on, an operation time may be stored in the memory (620) using a control timer (640), the controller (600) may check a threshold amount of time set in a predetermined cycle and compare an amount of operation time with the threshold amount of time in the memory (620) and, in a case in which a total amount of operation time exceeds the threshold amount of time, immediately turn off the power, and the controller (600) may be provided to, at the time of turning off the power, send information indicating the power being turned off to the outside through the communication device.

BRIEF DESCRIPTION OF THE DRAWINGS

The following drawings attached in this specification illustrate exemplary embodiments of the present disclosure and serve to provide better understanding of the technical spirit of the present disclosure along with the detailed description below, and thus the present disclosure should not be construed as being limited by the details shown in the drawings.

DETAILED DESCRIPTION OF EXEMPLARY EMBODIMENTS

Figure 1:
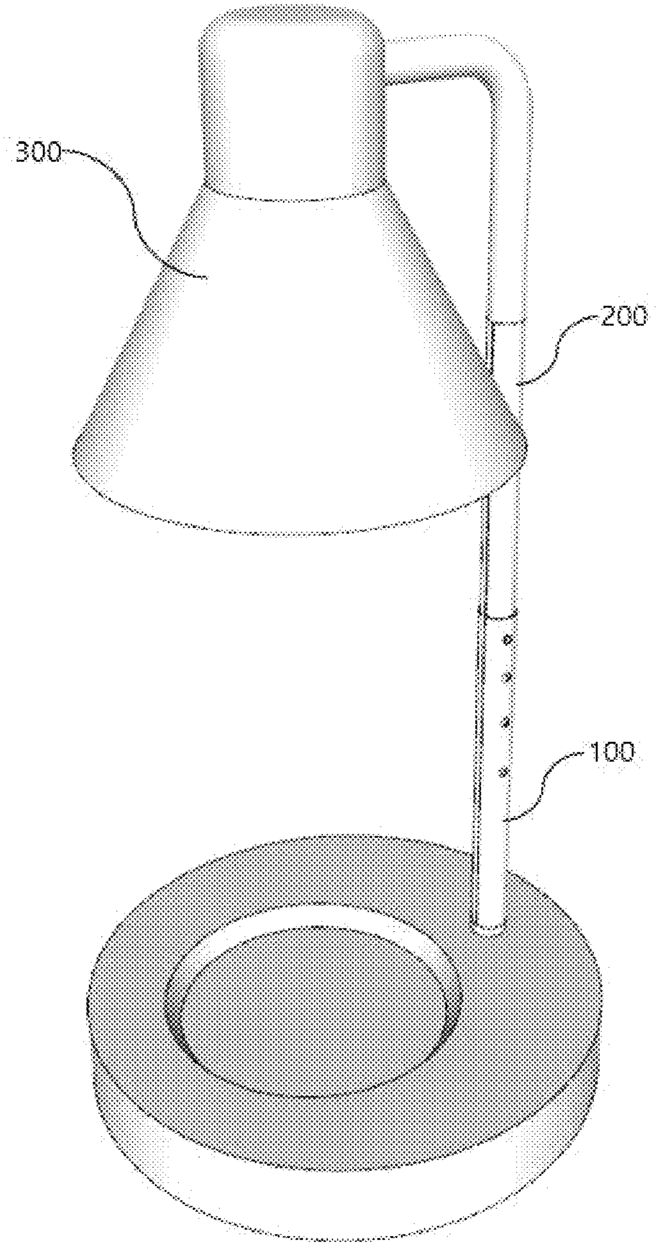
FIGS. 1 to 4 are 3D drawings for describing the overall configuration of a candle warmer with a height adjustment function according to an exemplary embodiment of the present disclosure.
Figure 2:
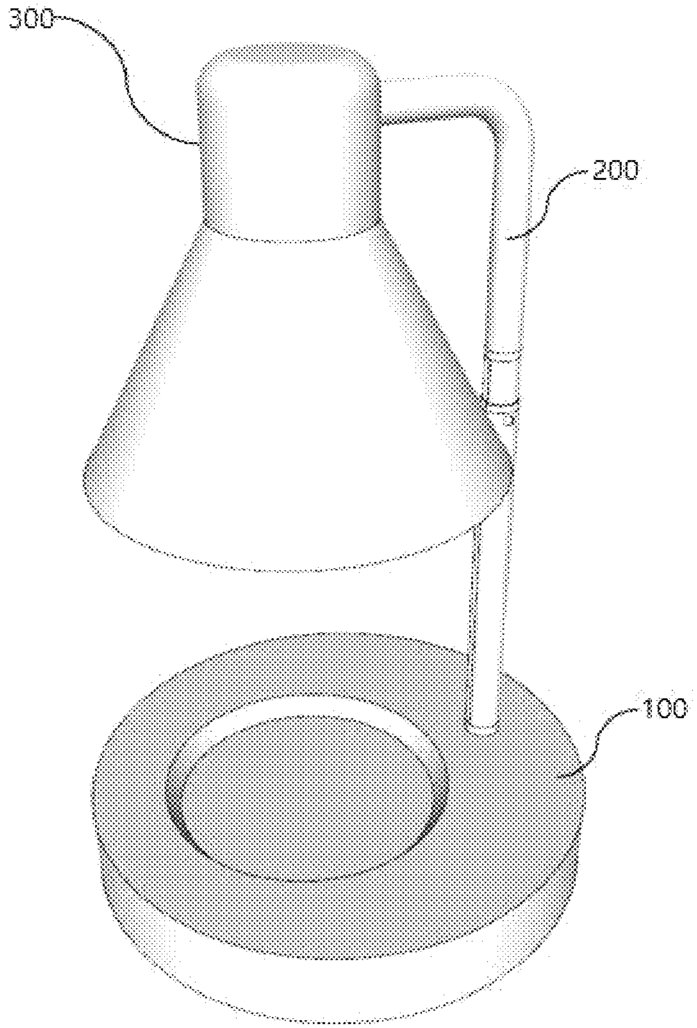
Figure 3:
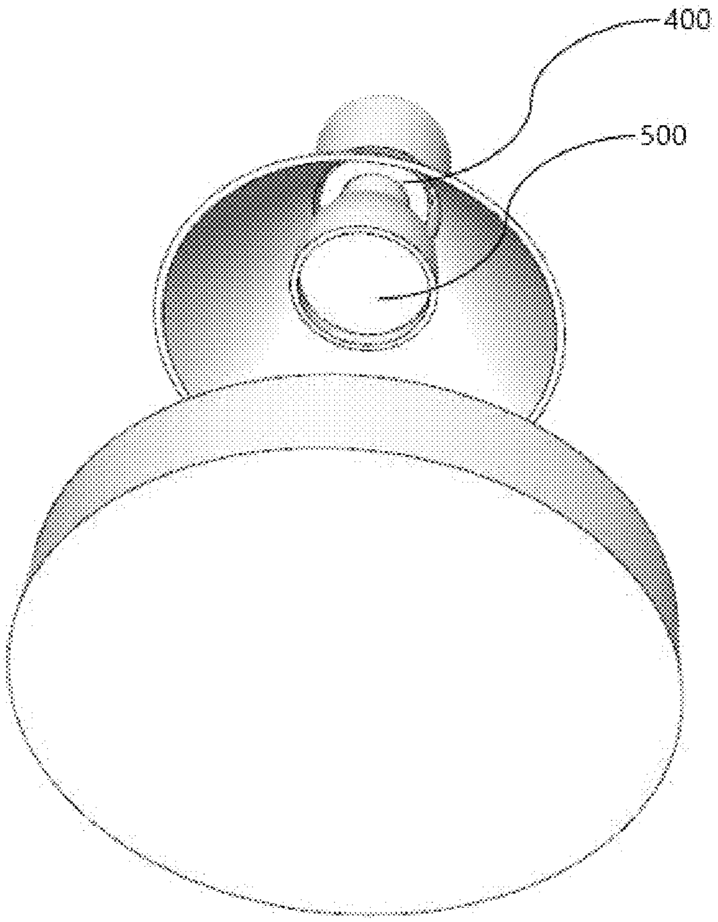
Figure 4:
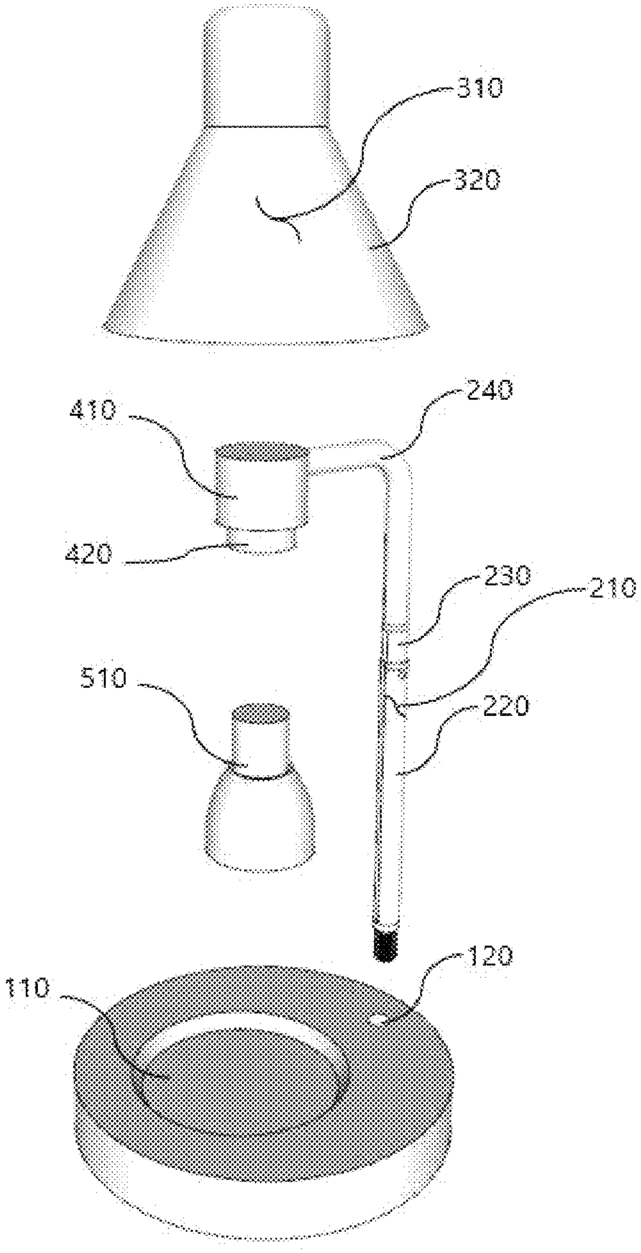
Figure 5:
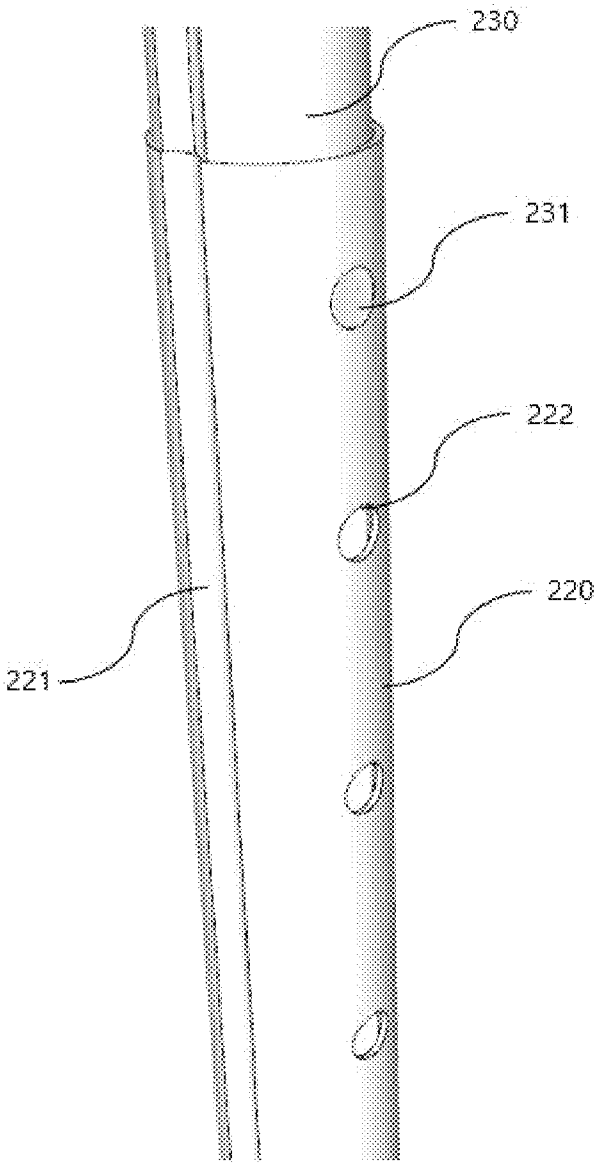
FIGS. 5 to 9 are 3D drawings for describing a height adjustment support of the candle warmer with a height adjustment function according to an exemplary embodiment of the present disclosure.
Figure 6:
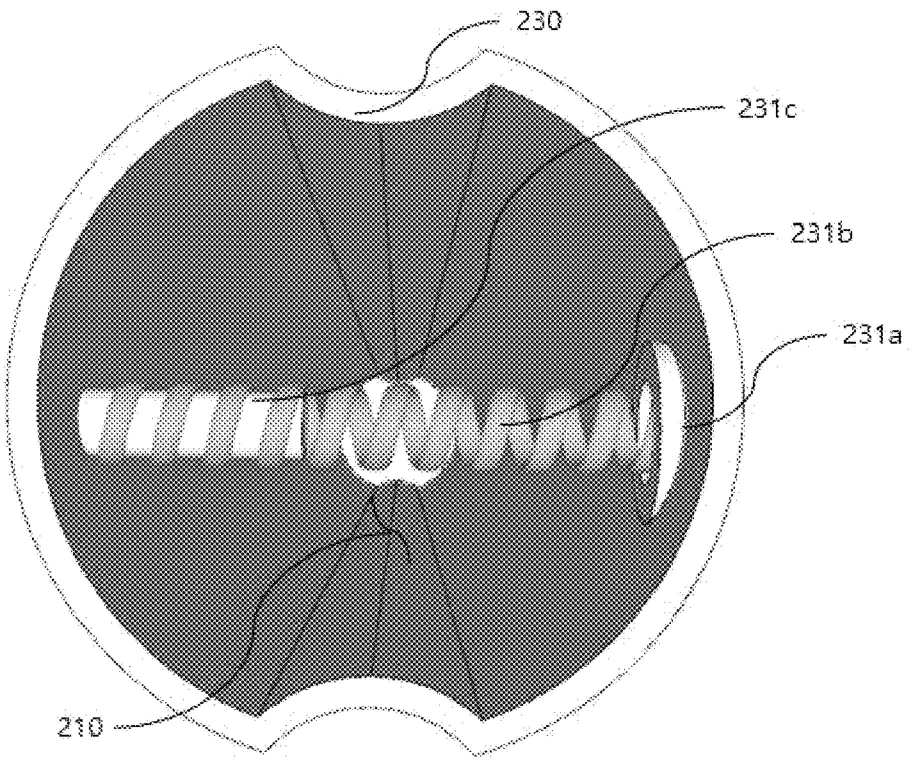
Figure 7:
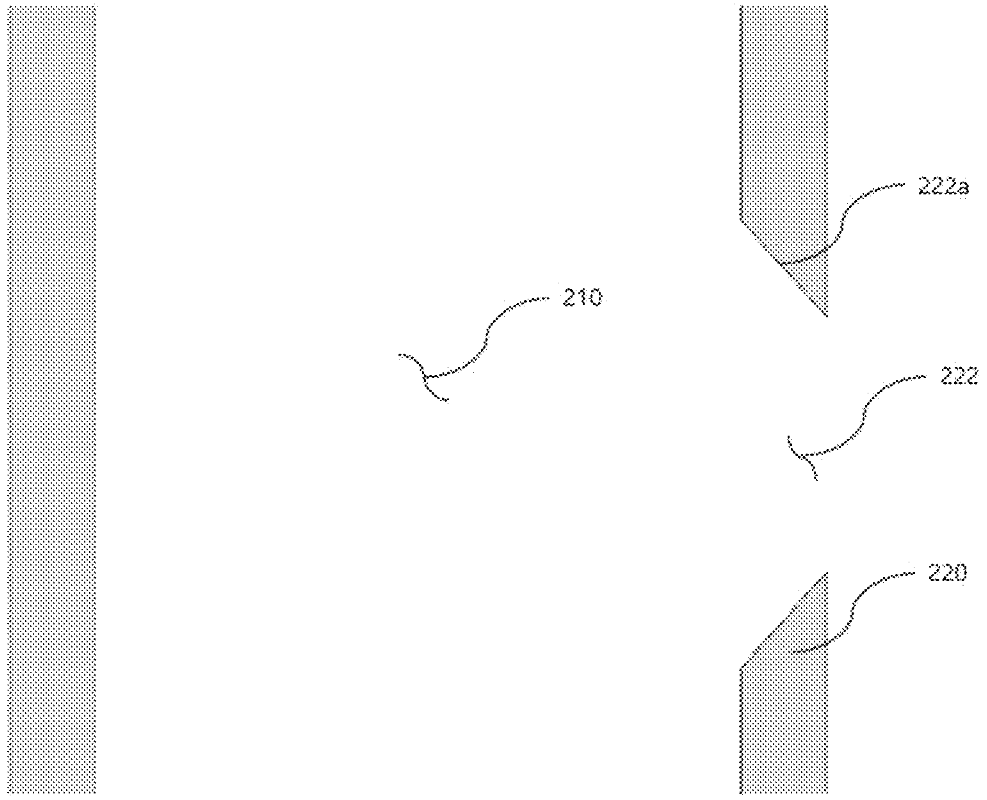
Figure 8:
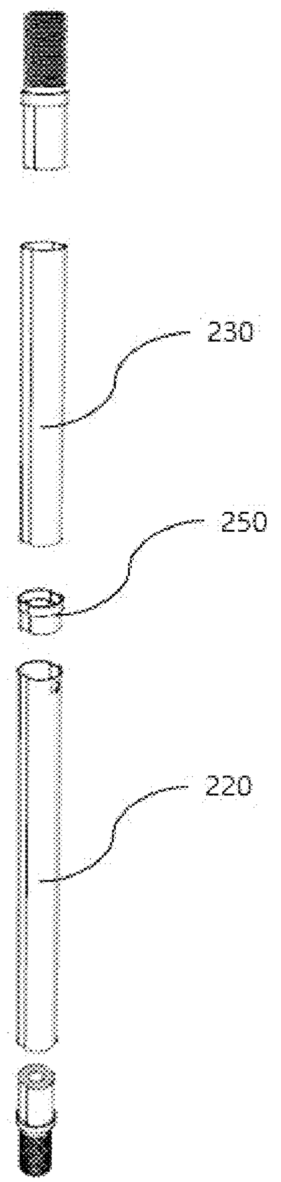
Figure 9:
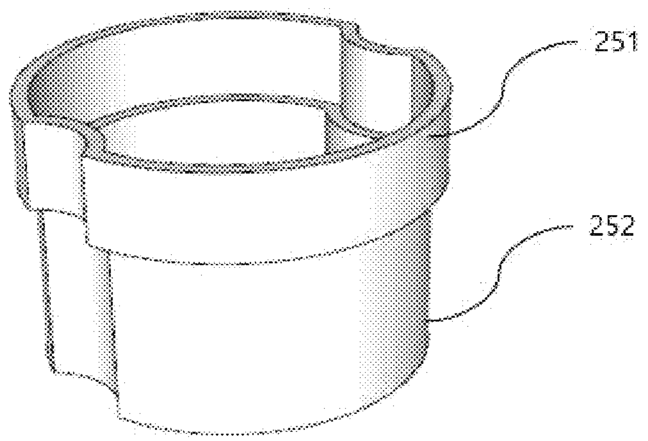

Specific structural or functional description of embodiments according to the concept of the present disclosure disclosed herein is only given for the purpose of describing embodiments according to the concept of the present disclosure. The embodiments according to the concept of the present disclosure may be embodied in various other forms and are not limited to the embodiments described herein.

The embodiments according to the concept of the present disclosure may be changed in various ways and have various forms. The embodiments illustrated in the drawings will be described in detail below. However, the detailed description is not intended to limit the embodiments according to the concept of the present disclosure to specific disclosed forms, and all changes, equivalents, or substitutes included in the spirit and technical scope of the present disclosure belong to the embodiments.

Figure 10:
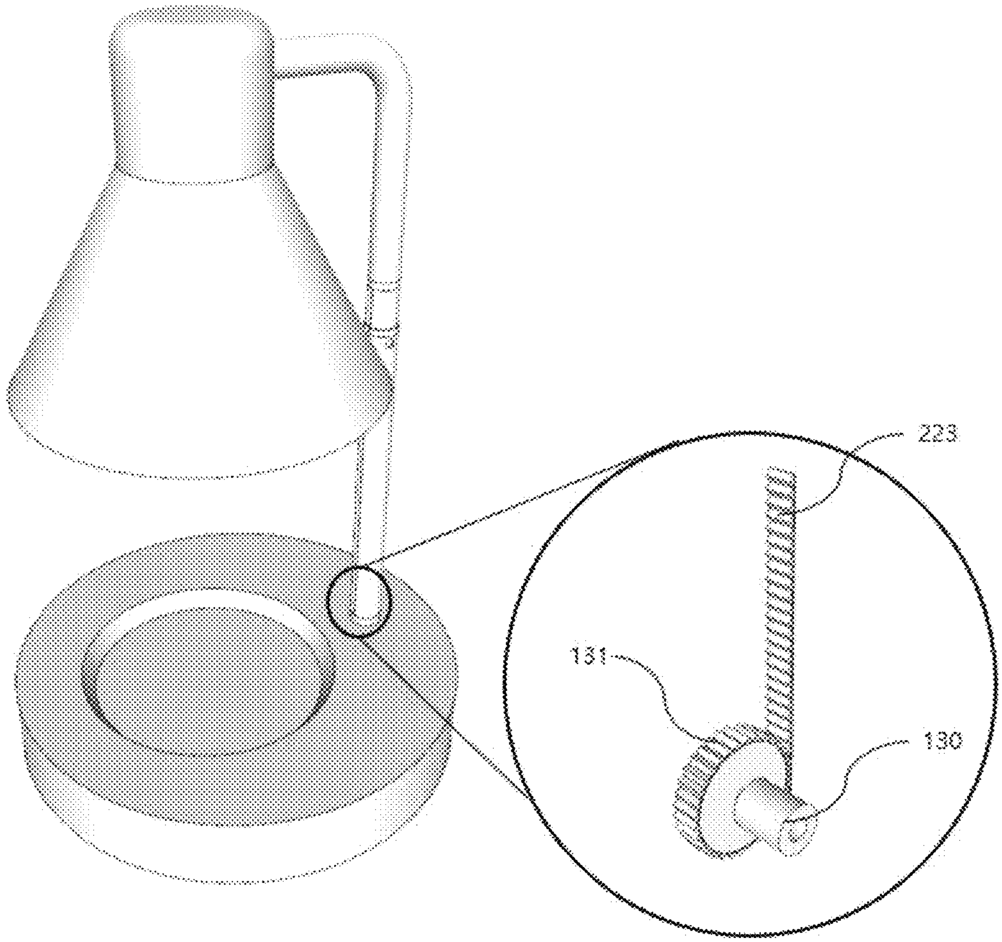
FIG. 10 is a 3D drawing for describing a gear of the candle warmer with a height adjustment function according to an exemplary embodiment of the present disclosure.
Figure 11:
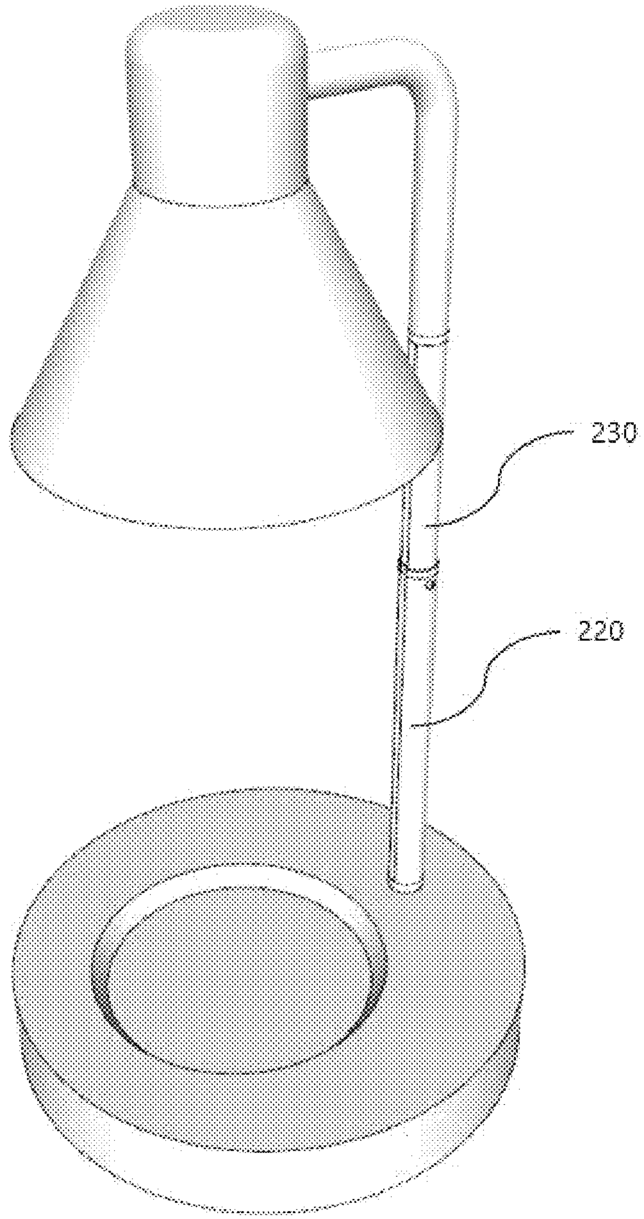
FIG. 11 is a 3D drawing for describing a use state of the candle warmer with a height adjustment function according to an exemplary embodiment of the present disclosure.
Figure 12:
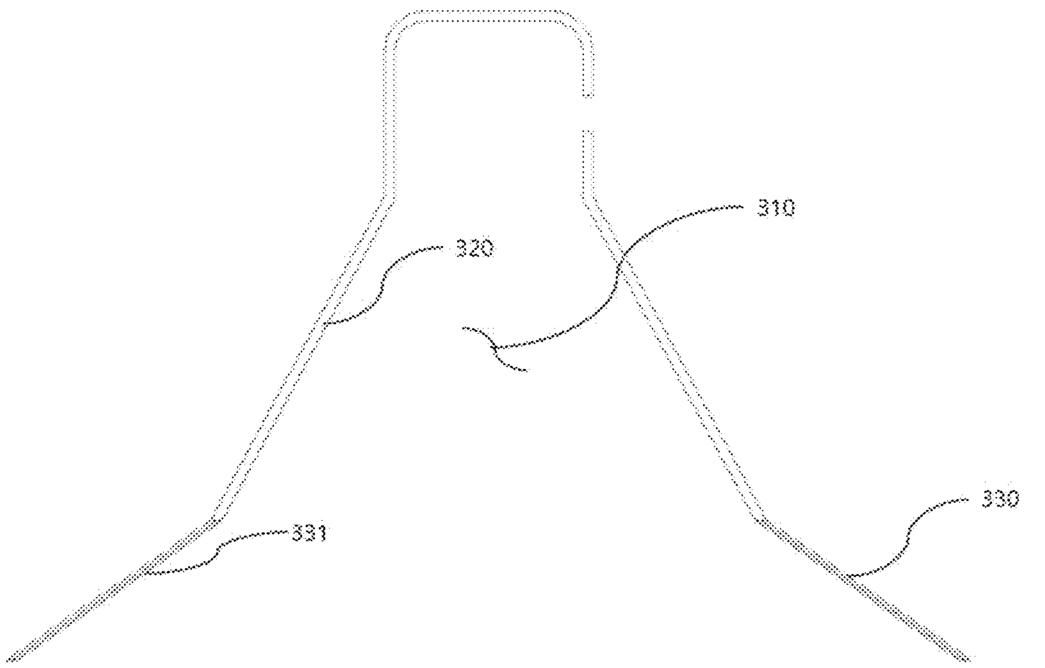
FIG. 12 is a 3D drawing for describing a heating shade of the candle warmer with a height adjustment function according to an exemplary embodiment of the present disclosure.
Figure 13:
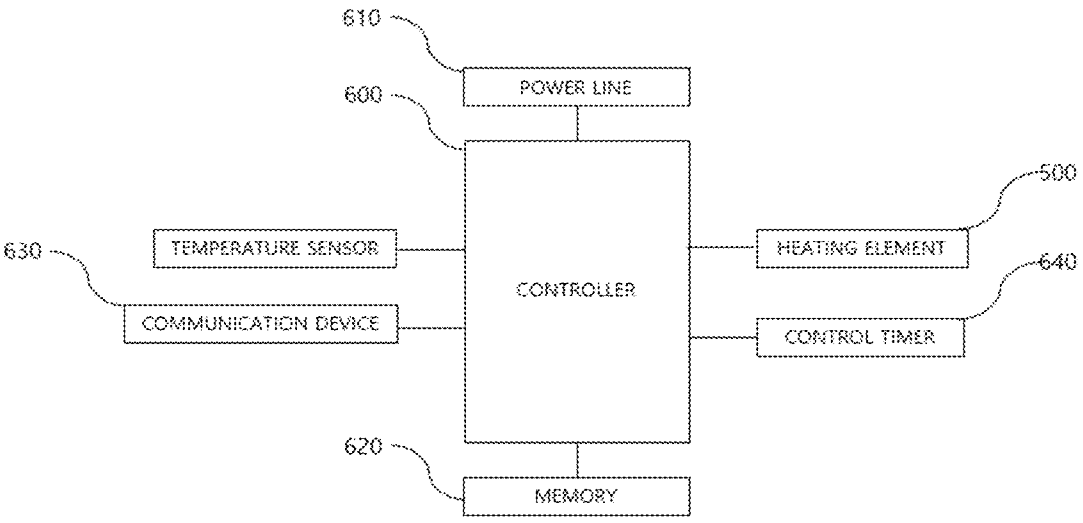
FIG. 13 is a block diagram for describing a controller of the candle warmer with a height adjustment function according to an exemplary embodiment of the present disclosure.

FIGS. 1 to 4 are 3D drawings for describing the overall configuration of a candle warmer with a height adjustment function according to an exemplary embodiment of the present disclosure, FIGS. 5 to 9 are 3D drawings for describing a height adjustment support of the candle warmer with a height adjustment function according to an exemplary embodiment of the present disclosure, FIG. 10 is a 3D drawing for describing a gear of the candle warmer with a height adjustment function according to an exemplary embodiment of the present disclosure, FIG. 11 is a 3D drawing for describing a use state of the candle warmer with a height adjustment function according to an exemplary embodiment of the present disclosure, FIG. 12 is a 3D drawing for describing a heating shade of the candle warmer with a height adjustment function according to an exemplary embodiment of the present disclosure, and FIG. 13 is a block diagram for describing a controller of the candle warmer with a height adjustment function according to an exemplary embodiment of the present disclosure.

A candle warmer with a height adjustment function according to one embodiment of the present disclosure that adjusts a height between a candle and a heating element to allow a user to flexibly correspond to various forms or types of scent-releasing candles used includes a base frame 100 having a candle mounting surface 110, on which a candle is mounted, provided at an upper portion.

Also, the candle warmer with a height adjustment function includes a height adjustment support 200 coupled in an upright state to an upper surface of the base frame 100 behind the candle mounting surface 110 and having a power line accommodation space 210 in which a power line 610, which is installed from a power source to a heating element 500, is accommodated.

In addition, the candle warmer with a height adjustment function includes a heating shade 300 which is connected to the height adjustment support 200 from above the height adjustment support 200 while being penetrated thereby, is formed in the shape of a bell, and has an accommodation space 310, which opens downward, provided at the center, and a heating element fixer 400 having a vertical fixer 420 provided to be fixed to the heating shade 300 through an upper fixer 410, which is disposed at the center of a bottom surface of an upper portion of the heating shade 300, to fix the heating element 500.

Here, the candle warmer with a height adjustment function includes the heating element 500 having a power connector 510, which is coupled to a longitudinal end of the vertical fixer 420 in a ground direction and connected to the power line 610, to generate heat toward a candle, and the heating element 500 may be changed to various forms such as a heating lamp and a heating wire.

Here, the candle warmer with a height adjustment function includes a controller 600 provided to control on or off of power and operation of the heating element 500 through the power line 610.

Here, the height adjustment support 200 includes a first support pipe 220 fixed in an upright state to a vertical coupling hole 120 disposed in the base frame 100, a second support pipe 230 inserted into the first support pipe 220 to allow a height to be adjustable, and a third support pipe 240 bent in an L-shape from a longitudinal end of the second support pipe 230 toward the heating shade 300.

Here, a semicircular guide groove 221 is formed inward in one side of at least any one of the first support pipe 220 and the second support pipe 230 to prevent twisting during vertical movement. A plurality of height adjustment holes 222 are formed at predetermined intervals in the first support pipe 220, the height adjustment holes 222 each have an inclined surface 222*a* to be inclined upward or downward in a direction from an outer circumferential surface of the first support pipe 220 toward an inner circumferential surface thereof, and a height adjustment protrusion 231 configured to protrude through the height adjustment hole 222 is provided on an outer circumferential surface of the second support pipe 230. In this way, height adjustment is possible.

That is, due to a pressing force exerted by a user gripping and pressing the second support pipe 230, the second support pipe 230 moves upward or downward, and the height is adjusted. The adjusted height is fixed by the height adjustment protrusion 231 partially protruding or being placed across the height adjustment hole 222.

Here, the height adjustment protrusion 231 includes a protruding surface 231*a*, an inner spring 231*b*, and a spring guider 231*c* configured to accommodate a portion of a longitudinal end of the inner spring 231*b*, and the spring guider 231*c* is fixed to an inner circumferential surface of the second support pipe 230. In this way, the spring is prevented from shaking and twisting.

Here, the spring guider 231*c* may surround the inner spring 231*b* from an inner side thereof as illustrated or may be provided in a cylindrical shape and surround the inner spring 231*b* from an outer side thereof.

Also, the height adjustment support 200 further includes an auxiliary sliding support pipe 250 which is inserted into the first support pipe 220 from above the first support pipe 220, has a hollow formed therein, and is made of a synthetic resin, and the second support pipe 230 is provided to be insertable into an upper portion of the auxiliary sliding support pipe 250.

Here, the auxiliary sliding support pipe 250 has a sliding protrusion 251 which is disposed at an upper end and protrudes more outward than an outer diameter of the second support pipe 230 and a sliding guide pipe 252 which is disposed below the sliding protrusion 251 and inserted into the first support pipe 220. In this way, during movement of the second support pipe 230, rigid movement is prevented to enable smooth vertical adjustment.

Meanwhile, a first gear 223 is disposed on the outer circumferential surface of the first support pipe 220, and a lifting/lowering motor 130 and a second gear 131 which rotates due to the lifting/lowering motor 130 and is engaged with the first gear 223 is further disposed on a bottom surface of the base frame (100) to allow the first support pipe 220 to move upward and downward while engaged with the first gear 223. In this way, according to temperature information collected by the controller 600, the lifting/lowering motor 130 is operated to control temperature and adjust scent release intensity.

Also, meanwhile, the upper fixer 410 includes a first fixer 411 coupled to the heating shade 300 while in contact therewith and a second fixer 412 configured to come in contact with a lower surface of the first fixer 411 and block heat of the heating element 500 from being transferred upward, and the vertical fixer 420 is provided to be vertically connected from a lower portion of the second fixer 412 to the heating element 500. In this way, heat is suppressed from being transferred upward.

Here, the heating shade 300 includes a first heating shade 320 configured to accommodate the heating element fixer 400 and the heating element 500 and a second heating shade 330 which extends downward from a lower edge of the first heating shade 320 and has an angle of inclination extending more outward than the first heating shade 320, and a heat reflecting shade 321 is further disposed at an inner side of the second heating shade 330. In this way, while heat is gathered toward the candle, the heat is prevented from being transferred outward.

Meanwhile, the controller 600 is provided to pre-store a threshold temperature in a memory 620, is provided to compare a temperature collected by a temperature sensor and the threshold temperature stored in the memory 620 and, in a case in which the collected temperature is higher than or equal to the threshold temperature, turn off the power, and is provided to send the collected temperature to the outside through a communication device 630. A maximum power-on time is pre-registered in the memory 620, and upon the power being turned on, an operation time is stored in the memory 620 using a control timer 640, the controller 600 checks a threshold amount of time set in a predetermined cycle and compares an amount of operation time with the threshold amount of time in the memory 620 and, in a case in which a total amount of operation time exceeds the threshold amount of time, immediately turns off the power, and the controller (600) is provided to, at the time of turning off the power, send information indicating the power being turned off to the outside through the communication device.

Using the candle warmer with a height adjustment function according to one embodiment of the present disclosure described above, by adjusting a height between a candle and a heating element, a user is allowed to flexibly correspond to various forms or types of scent-releasing candles used, and a scent release effect lasts by efficiently melting a candle even when the candle melts and shortens. Due to the base frame 100 having the candle mounting surface 110, on which a candle is mounted, provided at an upper portion, and the height adjustment support 200 coupled in an upright state to an upper surface of the base frame 100 behind the candle mounting surface 110 and having the power line accommodation space 210 in which the power line 610, which is installed from the power source to the heating element 500, is accommodated, the height can be conveniently adjusted according to a use state of the candle. Due to the heating shade 300 which is connected to the height adjustment support 200 from above the height adjustment support 200 while being penetrated thereby, is formed in the shape of a bell, and has the accommodation space 310, which opens downward, provided at the center, the heating element fixer 400 having the vertical fixer 420 provided to be fixed to the heating shade 300 through the upper fixer 410, which is disposed at the center of a bottom surface of the upper portion of the heating shade 300, to fix the heating element 500, and the heating element 500 having the power connector 510, which is coupled to the longitudinal end of the vertical fixer 420 in the ground direction and connected to the power line 610, to generate heat toward a candle, a heat radiation angle is firmly maintained, and energy efficiency is high. The height adjustment support 200 includes the first support pipe 220 fixed in an upright state to the vertical coupling hole 120 disposed in the base frame 100, the second support pipe 230 inserted into the first support pipe 220 to allow a height to be adjustable, and the third support pipe 240 bent in an L-shape from a longitudinal end of the second support pipe 230 toward the heating shade 300, wherein the semicircular guide groove 221 is formed inward in one side of at least any one of the first support pipe 220 and the second support pipe 230, and the plurality of height adjustment holes 222 are formed at predetermined intervals in the first support pipe 220 so that adjustment to various heights is possible by a simple operation. The height adjustment holes 222 each have the inclined surface 222*a* to be inclined upward or downward in the direction from the outer circumferential surface of the first support pipe 220 toward the inner circumferential surface thereof, the height adjustment protrusion 231 includes the protruding surface 231*a*, the inner spring 231*b*, and the spring guider 231*c* configured to accommodate a portion of the longitudinal end of the inner spring 231*b*, and the spring guider 231*c* is fixed to the inner circumferential surface of the second support pipe 230 so that smooth adjustment is possible. The height adjustment support 200 further includes the auxiliary sliding support pipe 250 which is inserted into the first support pipe 220 from above the first support pipe 220, has a hollow formed therein, and is made of a synthetic resin, the second support pipe 230 is insertable into the upper portion of the auxiliary sliding support pipe 250, and the auxiliary sliding support pipe 250 has the sliding protrusion 251 which is disposed at the upper end and protrudes more outward than the outer diameter of the second support pipe 230 and the sliding guide pipe 252 which is disposed below the sliding protrusion 251 and inserted into the first support pipe 220 so that smooth vertical movement is possible. The first gear 223 is disposed on the outer circumferential surface of the first support pipe 220, and the lifting/lowering motor 130 and the second gear 131 which rotates due to the lifting/lowering motor 130 and is engaged with the first gear 223 are disposed on the bottom surface of the base frame 100 to allow the first support pipe 220 to move upward and downward while engaged with the first gear 223 so that the controller 600 can adjust a height according to temperatures. The upper fixer 410 includes the first fixer 411 coupled to the heating shade 300 while in contact therewith and the second fixer 412 configured to come in contact with the lower surface of the first fixer 411 and block heat of the heating element 500 from being transferred upward, and the vertical fixer 420 is provided to be vertically connected from the lower portion of the second fixer 412 to the heating element 500, and thus an effect of transferring the heat downward and suppressing upward movement of the heat is expected.

The present disclosure provides a candle warmer with a height adjustment function, and first, by adjusting a height between a candle and a heating element, there is an effect of allowing a user to flexibly correspond to various forms or types of scent-releasing candles used and allowing a scent release effect to last by efficiently melting a candle even when the candle melts and shortens.

Second, due to a base frame 100 having a candle mounting surface 110, on which a candle is mounted, provided at an upper portion, and a height adjustment support 200 coupled in an upright state to an upper surface of the base frame 100 behind the candle mounting surface 110 and having a power line accommodation space 210 in which a power line 610, which is installed from a power source to a heating element 500, is accommodated, the height can be conveniently adjusted according to a use state of the candle.

Third, due to a heating shade 300 which is connected to the height adjustment support 200 from above the height adjustment support 200 while being penetrated thereby, is formed in the shape of a bell, and has an accommodation space 310, which opens downward, provided at the center, a heating element fixer 400 having a vertical fixer 420 provided to be fixed to the heating shade 300 through an upper fixer 410, which is disposed at the center of a bottom surface of an upper portion of the heating shade 300, to fix the heating element 500, and the heating element 500 having a power connector 510, which is coupled to a longitudinal end of the vertical fixer 420 in a ground direction and connected to the power line 610, to generate heat toward a candle, a heat radiation angle is firmly maintained, and energy efficiency is high.

Fourth, the height adjustment support 200 includes a first support pipe 220 fixed in an upright state to a vertical coupling hole 120 disposed in the base frame 100, a second support pipe 230 inserted into the first support pipe 220 to allow a height to be adjustable, and a third support pipe 240 bent in an L-shape from a longitudinal end of the second support pipe 230 toward the heating shade 300, wherein a semicircular guide groove 221 is formed inward in one side of at least any one of the first support pipe 220 and the second support pipe 230, and a plurality of height adjustment holes 222 are formed at predetermined intervals in the first support pipe 220. Therefore, adjustment to various heights is possible by a simple operation.

Fifth, the height adjustment holes 222 each have an inclined surface 222*a* to be inclined upward or downward in a direction from an outer circumferential surface of the first support pipe 220 toward an inner circumferential surface thereof, a height adjustment protrusion 231 configured to protrude through the height adjustment hole 222 is provided on an outer circumferential surface of the second support pipe 230, the height adjustment protrusion 231 includes a protruding surface 231*a*, an inner spring 231*b*, and a spring guider 231*c* configured to accommodate a portion of a longitudinal end of the inner spring 231*b*, and the spring guider 231*c* is fixed to an inner circumferential surface of the second support pipe 230. Therefore, smooth adjustment is possible.

Sixth, the height adjustment support 200 further includes an auxiliary sliding support pipe 250 which is inserted into the first support pipe 220 from above the first support pipe 220, has a hollow formed therein, and is made of a synthetic resin, the second support pipe 230 is insertable into an upper portion of the auxiliary sliding support pipe 250, and the auxiliary sliding support pipe 250 has a sliding protrusion 251 which is disposed at an upper end and protrudes more outward than an outer diameter of the second support pipe 230 and a sliding guide pipe 252 which is disposed below the sliding protrusion 251 and inserted into the first support pipe 220. Therefore, smooth vertical movement is possible.

Seventh, a first gear 223 is disposed on the outer circumferential surface of the first support pipe 220, and a lifting/lowering motor 130 and a second gear 131 which rotates due to the lifting/lowering motor 130 and is engaged with the first gear 223 are disposed on a bottom surface of the base frame 100 to allow the first support pipe 220 to move upward and downward while engaged with the first gear 223. Therefore, a controller 600 can adjust a height according to temperatures.

Eighth, the upper fixer 410 includes a first fixer 411 coupled to the heating shade 300 while in contact therewith and a second fixer 412 configured to come in contact with a lower surface of the first fixer 411 and block heat of the heating element 500 from being transferred upward, and the vertical fixer 420 is provided to be vertically connected from a lower portion of the second fixer 412 to the heating element 500. Therefore, there is an effect of transferring the heat downward and suppressing upward movement of the heat.

Meanwhile, advantageous effects of the present disclosure are not limited to those mentioned above, and other unmentioned advantageous effects should be clearly understood by those of ordinary skill in the art to which the present disclosure pertains from the description above.

Exemplary embodiments of the present disclosure have been described above. The embodiments described above are only illustrative of the technical spirit of the present disclosure, and those of ordinary skill in the art should understand that various changes are possible within the scope not departing from the technical spirit of the present disclosure. Therefore, the protection scope of the present disclosure should be construed according to details stated in the claims below instead of being construed according to specific embodiments, and any technical spirit within the scope equivalent to the claims should be construed as belonging to the scope of rights of the present disclosure.

What is claimed is:

1. A candle warmer with a height adjustment function, the candle warmer comprising:

a base frame having a candle mounting surface, on which a candle is mounted, provided at an upper portion;

a height adjustment support coupled in an upright state to an upper surface of the base frame behind the candle mounting surface and having a power line accommodation space in which a power line, which is installed from a power source to a heating element, is accommodated;

a heating shade which is connected to the height adjustment support from above the height adjustment support while being penetrated thereby, is formed in a shape of a bell, and has an accommodation space, which opens downward, provided at a center;

a heating element fixer having a vertical fixer provided to be fixed to the heating shade through an upper fixer, which is disposed at a center of a bottom surface of an upper portion of the heating shade, to fix the heating element;

the heating element having a power connector, which is coupled to a longitudinal end of the vertical fixer in a ground direction and connected to the power line, to generate heat toward a candle; and a controller provided to control on or off of power and operation of the heating element through the power line, wherein the height adjustment support includes a first support pipe fixed in an upright state to a vertical coupling hole disposed in the base frame, a second support pipe inserted into the first support pipe to allow a height to be adjustable, and a third support pipe bent in an L-shape from a longitudinal end of the second support pipe toward the heating shade, wherein a semicircular guide groove is formed inward in one side of at least any one of the first support pipe and the second support pipe, wherein a plurality of height adjustment holes are formed at predetermined intervals in the first support pipe, wherein the plurality of height adjustment holes each have an inclined surface to be inclined upward or downward in a direction from an outer circumferential surface of the first support pipe toward an inner circumferential surface thereof, wherein a height adjustment protrusion configured to protrude through a height adjustment hole is provided on an outer circumferential surface of the second support pipe, and wherein the height adjustment protrusion includes a protruding surface, an inner spring, and a spring guider configured to accommodate a portion of a longitudinal end of the inner spring, and the spring guider is fixed to an inner circumferential surface of the second support pipe.

2. The candle warmer of claim 1, wherein:

the height adjustment support further includes an auxiliary sliding support pipe which is inserted into the first support pipe from above the first support pipe, has a hollow formed therein, and is made of a synthetic resin, and the second support pipe is provided to be insertable into an upper portion of the auxiliary sliding support pipe, and the auxiliary sliding support pipe has a sliding protrusion which is disposed at an upper end and protrudes more outward than an outer diameter of the second support pipe and a sliding guide pipe which is disposed below the sliding protrusion and inserted into the first support pipe.

3. The candle warmer of claim 2, wherein:

a first gear is disposed on the outer circumferential surface of the first support pipe, and a lifting/lowering motor and a second gear which rotates due to the lifting/lowering motor and is engaged with the first gear are further disposed on a bottom surface of the base frame to allow the first support pipe to move upward and downward while engaged with the first gear;

a temperature sensor is further disposed in the controller; and a height of the heating shade is changeable by the controller rotating the lifting/lowering motor according to a temperature collected by the temperature sensor.

4. The candle warmer of claim 1, wherein:

the upper fixer includes a first fixer coupled to the heating shade while in contact therewith and a second fixer configured to come in contact with a lower surface of the first fixer and block heat of the heating element from being transferred upward; and the vertical fixer is provided to be vertically connected from a lower portion of the second fixer to the heating element.

5. The candle warmer of claim 2, wherein the heating shade includes a first heating shade configured to accommodate the heating element fixer and the heating element and a second heating shade which extends downward from a lower edge of the first heating shade and has an angle of inclination extending more outward than the first heating shade, and a heat reflecting shade is further disposed at an inner side of the second heating shade.

6. The candle warmer of claim 1, wherein the controller is provided to pre-store a threshold temperature in a memory, is provided to compare a temperature collected by a temperature sensor and the threshold temperature stored in the memory and, in a case in which the collected temperature is higher than or equal to the threshold temperature, turn off the power, and is provided to send the collected temperature to an external receiver through a communication device, a maximum power-on time is pre-registered in the memory, and upon the power being turned on, an operation time is stored in the memory using a control timer, the controller checks a threshold amount of time set in a predetermined cycle and compares an amount of operation time with the threshold amount of time in the memory and, in a case in which a total amount of operation time exceeds the threshold amount of time, immediately turns off the power, and the controller is provided to, at the time of turning off the power, send information indicating the power being turned off to the external receiver through the communication device.

* * * * *